United States Patent [19]
Harada et al.

[11] Patent Number: 4,476,318
[45] Date of Patent: Oct. 9, 1984

[54] PROCESS FOR THE PREPARATION OF 1,3-PROPANEDIOL BIS(P-AMINOBENZOATE)

[75] Inventors: Takao Harada, Shizuoka; Chihiro Yazawa, Kanagawa, both of Japan

[73] Assignee: Ihara Chemical Industry Co., Ltd., Tokyo, Japan

[21] Appl. No.: 428,518

[22] Filed: Sep. 29, 1982

[30] Foreign Application Priority Data

Oct. 6, 1981 [JP] Japan .............................. 56-159596

[51] Int. Cl.³ .................. C07C 101/00; C07C 69/76; C07C 101/48
[52] U.S. Cl. ..................................... 560/50; 560/112; 562/458
[58] Field of Search .................. 560/50, 112; 562/437

[56] References Cited
U.S. PATENT DOCUMENTS 4,058,550 11/1977 Shepherd et al. ..................... 560/43

OTHER PUBLICATIONS

Noller, Chemistry of Organic Compounds, W. B. Saunders Co., 1965, pp. 185–186.
Yoneda et al., J. Chem. Soc. Japan, Ind. Chem. Sec., 69, 641-3 (1966), as Abstracted p. A38.

Primary Examiner—Natalie Trousof
Assistant Examiner—Bruce D. Gray
Attorney, Agent, or Firm—Sughrue, Mion, Zinn, MacPeak & Seas

[57] ABSTRACT

A process for the preparation of 1,3-propanediol bis(p-aminobenzoate) is described, comprising reacting a p-aminobenzoic acid alkali metal salt with dihalogenated propane in an aprotic polar solvent. In accordance with this process, diesterification proceeds under mild conditions without causing any undesirable side reactions and, therefore the desired 1,3-propanediol bis(p-aminobenzoate) can be obtained in high purity and high yield.

4 Claims, No Drawings

PROCESS FOR THE PREPARATION OF 1,3-PROPANEDIOL BIS(P-AMINOBENZOATE)

FIELD OF THE INVENTION

The present invention relates to an improved process for the preparation of 1,3-propanediol bis(p-aminobenzoate) which is useful as a hardener for the production of polyurethane elastomer.

BACKGROUND OF THE INVENTION

Various methods have been proposed for the preparation of alkanediol bis(aminobenzoate) such as 1,3-propanediol bis(p-aminobenzoate), including:

(1) a method in which nitrobenzoic acid chloride is reacted with an alkanediol in a pyridine solvent to prepare alkanediol bis(nitrobenzoate), and the alkanediol bis(nitrobenzoate) thus prepared is then reduced with hydrazine in the presence of a palladium or charcoal catalyst in an ethanol solvent (Japanese Patent Publication No. 10030/79 (corresponding to U.S. Pat. No. 3,932,360));

(2) a method in which nitrobenzoic acid and alkanediol are reacted in an anisole solvent to prepare alkanediol bis(nitrobenzoate), and the alkanediol bis(nitrobenzoate) is hydrogenated in the presence of a palladium-carbon catalyst (DE-OS No. 2,853,175 (corresponding to U.S. Pat. No. 4,283,549)); and (3) a method in which nitrobenzoic acid and alkanediol are reacted in the presence of a p-toluenesulfonic acid catalyst without the use of a solvent to prepare alkanediol bis(nitrobenzoate), and the thus-formed alkanediol bis(nitrobenzoate) is hydrogenated in a methanol solvent in the presence of nickel and sodium dihydrogenphosphate (European Patent Application Laid-Open No. 13,956).

The method (1), however, has disadvantages in that it involves two steps of esterification and reduction, the yield of the desired alkanediol bis(aminobenzoate) is as low as 63% (esterification yield: 84%; reduction yield: 75%), and in that use is made of hydrazine which requires strict care in the handling thereof. Therefore, this method is not suitable for use in the commercial preparation of alkanediol bis(aminobenzoate).

The methods (2) and (3) have been developed in order to overcome the problems of the method (1). These methods, however, also suffer from disadvantages in that they involve two steps of esterification and reduction, the esterification and reduction reactions should be made at high temperatures for long periods of time—e.g., at 180°-190° C. for 6 hours and 160° C. for 4 hours (under reduced pressure for 1 hour), respectively—in order to increase the esterification yield, and in that complicated operations are needed in the handling of hydrogen (since the reduction is achieved by hydrogenation), the recovery of the catalyst, and so forth. Thus, none of the methods are satisfactory as an industrial method of production of alkanediol bis(p-aminobenzoate).

In addition, there may be considered another method of production of alkanediol bis(aminobenzoate) which comprises reacting aminobenzic acid or its metal salt with dihalogenated alkane. In accordance with this method, however, since aminobenzoic acid or its metal salt contains an amino group and a carboxyl group or carboxylate group (-COOM) as active groups which react with the dihalogenated alkane, side reactions such as N-alkylation as well as the main reaction of esterification occur, producing various by-products. It is therefore impossible to prepare the desired alkanediol bis(aminobenzoate) in high purity and high yield.

In view of the various disadvantages of any one of the methods described above, there is clearly a need to develop a new method for preparing alkanediol bis(aminobenzoate).

SUMMARY OF THE INVENTION

The present inventors have carried out extensive investigations to develop a process for the preparation of alkanediol bis(p-aminobenzoate) which is free from the above-described defects of the prior art methods. As a result, they have found that when p-aminobenzoic acid alkali metal salts and 1,3-dihalogenated propane are used as starting materials and reacted in an aprotic polar solvent, side reactions are greatly reduced and diesterification proceeds under mild conditions. Therefore, the desired 1,3-propanediol bis(p-aminobenzoate) can be obtained in high purity and high yield.

The present invention relates to a process for the preparation of 1,3-propanediol bis(p-aminobenzoate) represented by the general formula (III):

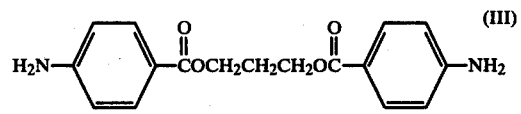

which comprises reacting a p-aminobenzoic acid alkali metal salt represented by the general formula (I):

(wherein M is an alkali metal atom) with dihalogenated propane represented by the general formula (II):

(wherein X and Y may be the same or different, and are halogen atoms) in an aprotic polar solvent.

DETAILED DESCRIPTION OF THE INVENTION p-Aminobenzoic acid alkali metal salts represented by the general formula (I) include sodium p-aminobenzoate and potassium p-aminobenzoate. When p-aminobenzoic acid alkaline earth metal salts such as calcium p-aminobenzoate and barium p-aminobenzoate, and other metal salts are used in place of such p-aminobenzoic acid alkali metal salts, the reaction does not proceed smoothly and the desired 1,3-propanediol bis(p-aminobenzoate) cannot be obtained in high purity and high yield. If desired, the p-aminobenzoic acid alkali metal salt of the invention can be easily obtained by reacting p-aminobenzoic acid with a corresponding alkali metal base, prior to subjecting to the reaction of this invention.

Examples of the dihalogenated propanes represented by the general formula (II) include 1,3-dichloropropane, 1,3-dibromopropane, and 1-bromo-3-chloropropane.

The reaction between the p-aminobenzoic acid alkali metal salt and dihalogenated alkane in an aprotic polar solvent proceeds specifically only when the dihalogenated alkane is dihalogenated propane represented by the general formula (II), and it does not proceed smoothly when dihalogenated alkanes such as 1,2-dichloropropane, 1,2-dichloroethane, 1,4-dichlorobutane, 1,5-dichloropentane, and 1,8-dichlorooctane are used.

Aprotic polar solvents which can be used in the invention include dimethylformamide, dimethylacetamide, dimethyl sulfoxide, tetramethylurea, hexamethylphosphoramide, sulfolane, and N-methylpyrrolidone. When non-polar solvents such as benzene, toluene, xylene, chlorobenzene, and chlorotoluene, or polar solvents such as acetonitrile, ethylene glycol, glycerine, diglyme, and nitrobenzene are used in place of the aprotic polar solvents of the invention, the reaction almost does not proceed and the desired 1,3-propanediol bis(p-aminobenzoate) cannot be obtained.

In accordance with the process of the invention, as described hereinbefore, the p-aminobenzoic acid alkali metal salt of the general formula (I) and dihalogenated propane of the general formula (II) are reacted in the aprotic polar solvent while heating and stirring. This reaction can be represented by the following reaction formula:

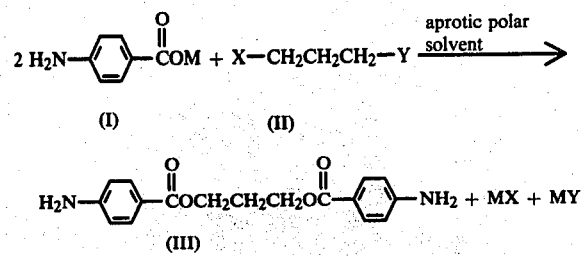

The reaction between the p-aminobenzoic acid alkali metal salt and dihalogenated propane can be performed either by a method in which the p-aminobenzoic acid alkali metal salt and dihalogenated propane are charged to a reactor along with the aprotic polar solvent and reacted while heating and stirring, or by a method in which the p-aminobenzoic acid alkali metal salt is charged to a reactor along with the aprotic polar solvent and, with heat-stirring, the dihalogenated propane is added dropwise thereto to proceed the reaction therebetween. That is, any method can be employed as long as the p-aminobenzoic acid alkali metal salt and dihalogenated propane can be reacted in the aprotic polar solvent while heating and stirring.

The reaction temperature is usually from 60° to 150° C. and preferably from 80° to 130° C. When the reaction temperature is lower than 60° C., the reaction proceeds very slowly and it does not proceed to a sufficient extent even after 24 hours. On the other hand, when the reaction temperature exceeds 150° C., side reactions such as N-alkylation undesirably occur.

The reaction time varies with the reaction temperature—e.g., as the reaction temperature is increased, the reaction time is shortened—and it is sufficient to be from 1 to 6 hours at a temperature of from 80° to 130° C.

The molar ratio of the p-aminobenzoic acid alkali metal salt to the dihalogenated propane is sufficient to be 2 according to the above-described reaction formula, but it is usually in a range of from 2:1 to 5:1, preferably from 2:1 to 3:1. Addition of the p-aminobenzoic acid alkali metal salt at a molar ratio exceeding 5—i.e., the use of an excess amount of p-aminobenzoic acid alkali metal salt—does not appreciably increase the yield and, therefore, is not economical.

The aprotic polar solvent is used in such an amount as to permit sufficient stirring of the reaction mixture. It is sufficient for the aprotic polar solvent to be used in an amount from 3 to 5 times (by weight) the p-aminobenzoic acid alkali metal salt.

From the thus-obtained reaction mixture can be obtained the desired 1,3-propanediol bis(p-aminobenzoate) by usual techniques such as a method in which the reaction solvent is distilled away, the residue is poured into water to precipitate crystals, and thereafter, the crystals are collected by filtration and dried, and a method in which after the reaction solvent is distilled away, a water-insoluble solvent, such as ethylene chloride, dichloroethane, chlorobenzene, and dichlorobenzene, is added and water-washing is performed, and thereafter, crystals are recrystallized, collected by filtration, and dried.

One of the features of the process of the invention is that high purity 1,3-propanediol bis(p-aminobenzoate) can be prepared in high yield while inhibiting side reactions by reacting p-aminobenzoic acid alkali metal salt and dihalogenated propane in an aprotic polar solvent. Further, the process of the invention presents the advantage that the desired product can be prepared by a simple and safe procedure and economically compared with the conventional methods. Thus, the process of the invention is very useful as a process for the commercial production of 1,3-propanediol bis(p-aminobenzoate).

The following examples and comparative examples are given to illustrate the invention in greater detail.

EXAMPLE 1

A 500-ml four-necked flask equipped with a thermometer, a condenser and a stirrer was charged with 200 g of dimethyl sulfoxide, 47.7 g (0.3 mole) of sodium p-aminobenzoate, and 16.9 g (0.15 mole) of 1,3-dichloropropane, which were then reacted at 100° C. for 3 hours while heating and stirring.

After the reaction was completed, the dimethyl sulfoxide was distilled away under reduced pressure from the reaction mixture, and thereafter, 200 g of ethylene chloride, 100 ml of water, and 0.7 g of sodium carbonate were added to the residue. The resulting mixture was separated. Water-washing and separation was repeated twice using 100 ml of hot water maintained at 70° C. The thus-obtained organic layer was cooled to room temperature to precipitate crystals. The crystals thus obtained were collected by filtration and dried to obtain 43.1 g of 1,3-propanediol bis(p-aminobenzoate), pale yellow crystals having a melting point of 123°–127° C. (yield, 91.5%). High performance Liquid Chromatographic analysis showed that the purity was 97.4%.

EXAMPLE 2

A 1-liter four-necked flask equipped with a thermometer, a condenser and a stirrer was charged with 400 g of dimethylformamide, 105.2 g (0.6 mole) of potassium p-aminobenzoate, and 47.2 g (0.3 mole) of 1-bromo-3-chloropropane, which were then reacted at 120° C. for 1 hour while heating and stirring.

After the reaction was completed, the dimethylformamide was distilled away under reduced pressure from the reaction mixture, and thereafter, 400 g of o-dichlorobenzene, 200 ml of water, and 1.4 g of sodium carbonate were added to the resulting residue. The mixture was separated. Water-washing and separation was repeated twice using 200 ml of hot water maintained at 70° C. The thus-obtained organic layer was cooled to room temperature to precipitate crystals. These crystals were collected by filtration and dried to obtain 85.6 g of 1,3-propanediol bis(p-aminobenzoate), pale yellow crystals having a melting point of 123°–127° C. (yield: 90.8%). High Performance Liquid Chromatographic analysis showed that the purity was 97.1%.

EXAMPLES 3 to 8

1,3-Propanediol bis(p-aminobenzoate) was prepared in the same manner as in Example 1 except that various aprotic polar solvents were used in place of dimethyl sulfoxide. The results are shown in Table 1.

TABLE 1

| Example | Solvent | 1,3-Propanediol bis-(p-aminobenzoate) | | |
|---|---|---|---|---|
| | | Amount (g) | Yield (%) | Purity (%) |
| 1 | dimethyl sulfoxide | 43.1 | 91.5 | 97.4 |
| 3 | dimethylformamide | 43.3 | 91.8 | 97.2 |
| 4 | dimethylacetamide | 43.5 | 92.3 | 97.0 |
| 5 | tetramethylurea | 41.5 | 88.0 | 95.2 |
| 6 | hexamethylphosphoramide | 43.1 | 91.5 | 96.8 |
| 7 | sulfolane | 41.6 | 88.3 | 94.5 |
| 8 | N—methylpyrrolidone | 42.8 | 90.8 | 96.6 |

COMPARATIVE EXAMPLES 1 to 6

The procedure of Example 1 was repeated wherein o-chlorotoluene, chlorobenzene, ethylene glycol, glycerine, diglyme or nitrobenzene was used in place of dimethyl sulfoxide and that the reaction temperature and time were changed to 120° C. and 10 hours, respectively. The results are shown in Table 2.

COMPARATIVE EXAMPLES 7 to 9

The procedure of Example 1 was repeated wherein 23.6 g (0.15 mole) of 1-bromo-3-chloropropane was used in place of 16.9 g (0.15 mole) of 1,3-dichloropropane, ethylene glycol, glycerine, or diglyme was used in place of dimethyl sulfoxide, the reaction temperature was changed to 150° C., and the reaction time was changed to 10 hours. The results are shown in Table 2.

TABLE 2

| Comparative Example | Solvent | Dihalogenated Propane | Temperature (°C.) | Time (hr) | Dialkanediol bis-(p-aminobenzoate) | | |
|---|---|---|---|---|---|---|---|
| | | | | | Amount (g) | Yield (%) | Purity (%) |
| 1 | o-chlorotoluene | 1,3-dichloropropane | 120 | 10 | 0 | 0 | — |
| 2 | chlorobenzene | " | 120 | 10 | 0 | 0 | — |
| 3 | ethylene glycol | " | 120 | 10 | 1.4 | 3 | 85.0 |
| 4 | glycerine | " | 120 | 10 | 0 | 0 | — |
| 5 | diglyme | " | 120 | 10 | 0 | 0 | — |
| 6 | nitrobenzene | " | 120 | 10 | 0 | 0 | — |
| 7 | ethylene glycol | 1-bromo-3-chloropropane | 150 | 10 | 2.4 | 5 | 83.0 |
| 8 | glycerine | " | 150 | 10 | 0 | 0 | — |
| 9 | diglyme | " | 150 | 10 | 0 | 0 | — |

EXAMPLE 9

A 300-ml four-necked flask equipped with a thermometer, a condenser and a stirrer was charged with 130 g of dimethylformamide, 31.8 g (0.2 mole) of sodium p-aminobenzoate, and 11.3 g (0.1 mole) of 1,3-dichloropropane, which were then reacted at 120° C. for 3 hours while heating and stirring.

After the reaction was completed, the dimethylformamide was distilled away under reduced pressure from the reaction mixture, and thereafter, the residue was poured into 300 ml of water with stirring to precipitate crystals. These crystals were collected by filtration, washed with water, and dried to obtain 29.9 g of 1,3-propanediol bis(p-aminobenzoate), pale yellow crystals having a melting point of 120°–125° C. (yield: 95%).

COMPARATIVE EXAMPLES 10 to 14

The procedure of Example 9 was repeated wherein various dihalogenated alkanes were used in place of 1,3-dichloropropane. The results are shown in Table 3.

TABLE 3

| | Dihalogenated Alkane | Alkanediol bis-(p-aminobenzoate) | | |
|---|---|---|---|---|
| | | Amount (g) | Yield (%) | Purity (%) |
| Example 9 | 1,3-dichloropropane | 29.9 | 95.0 | 95.1 |
| Comparative Example 10 | 1,2-dichloroethane | 10.8 | 34.2 | 82.5 |
| Example 11 | 1,4-dichlorobutane | 17.3 | 55.1 | 88.3 |
| Example 12 | 1,5-dichloropentane | 14.8 | 47.0 | 88.5 |
| Example 13 | 1,8-dichlorooctane | 14.7 | 46.8 | 86.4 |
| Example 14 | 1,2-dichloropropane | 0 | 0 | — |

EXAMPLES 10 to 14 AND COMPARATIVE EXAMPLES 15 to 16

The procedure of Example 1 was repeated wherein the reaction temperature and the reaction time were changed as shown in Table 4. The results are shown in Table 4.

TABLE 4

| | Reaction Temperature (°C.) | Reaction Time (hr) | 1,3-Propanediol bis-(p-aminobenzoate) | | |
|---|---|---|---|---|---|
| | | | Amount (g) | Yield (%) | Purity (%) |
| Example 10 | 80 | 6 | 42.4 | 89.9 | 97.2 |
| Example 11 | 90 | 5 | 43.2 | 91.6 | 97.4 |
| Example 12 | 100 | 4 | 43.3 | 91.8 | 97.4 |
| Example 13 | 110 | 2 | 42.8 | 90.9 | 97.8 |
| Example 14 | 130 | 1 | 42.9 | 91.0 | 97.5 |
| Comparative Example 15 | 50 | 10 | 12.5 | 26.5 | 76.5 |
| Example 16 | 160 | 1 | 42.2 | 89.5 | 88.4 |

COMPARATIVE EXAMPLE 17

The procedure of Example 1 was repeated wherein 33.6 g (0.15 mole) of calcium p-aminobenzoate was used in place of 47.7 g (0.3 mole) of sodium p-aminobenzoate. The reaction, however, almost did not proceed and the desired 1,3-propanediol bis(p-aminobenzoate) was almost not obtained.

While the invention has been described in detail and with reference to specific embodiments thereof, it will be apparent to one skilled in the art that various changes and modifications can be made therein without departing from the spirit and scope thereof.

What is claimed is:

1. A process for preparing 1,3-propanediol bis(p-aminobenzoate) represented by formula (III):

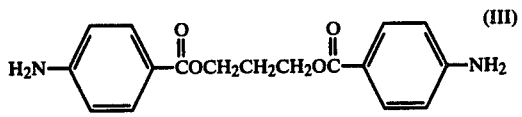

comprising reacting (i) a p-aminobenzoic acid alkali metal salt represented by formula (I):

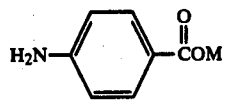

(wherein M is an alkali metal atom) with (ii) dihalogenated propane represented by formula (II):

$$X-CH_2CH_2CH_2-Y \qquad (II)$$

(wherein X and Y may be the same or different, and are halogen atoms), in an aprotic polar solvent and at a temperature of from 60° C. to 150° C.

2. A process for preparing 1,3-propanediol bis(p-aminobenzoate) as claimed in claim 1, wherein the reaction is carried out at a temperature of from 80° C. to 130° C.

3. A process for preparing 1,3-propanediol bis(p-aminobenzoate) as claimed in claim 2, wherein the reaction is carried out over a period of from 1 hour to 6 hours.

4. A process for preparing 1,3-propanediol bis(p-aminobenzoate) as claimed in any one of claims 1 or 3, wherein the aprotic polar solvent is present in an amount of 3 to 5 times by weight the amount of the p-aminobenzoic acid alkali metal salt.

* * * * *